United States Patent [19]

Garcia et al.

[11] Patent Number: 4,637,403
[45] Date of Patent: Jan. 20, 1987

[54] GLUCOSE MEDICAL MONITORING SYSTEM

[75] Inventors: Fernando S. Garcia; Hartmut Ginnow-Merkert; Paul J. Anderson; Bertram J. Hudson, all of Eden Prairie, Minn.

[73] Assignee: Garid, Inc., Eden Prairie, Minn.

[21] Appl. No.: 744,539

[22] Filed: Jun. 14, 1985

Related U.S. Application Data

[63] Continuation-in-part of Ser. No. 720,906, Apr. 8, 1985.

[51] Int. Cl.⁴ .............................................. A61B 17/3
[52] U.S. Cl. ............................... 128/770; 128/329 R; 128/637
[58] Field of Search ............... 128/303 R, 329 R, 760, 128/763, 767, 770, 771, 633, 636, 637; 73/864.87, 61.1 C; 356/39-42

[56] References Cited

U.S. PATENT DOCUMENTS

| | | | |
|---|---|---|---|
| 4,003,707 | 1/1977 | Lubbers et al. | 356/39 |
| 4,257,427 | 3/1981 | Bucalo | 128/769 |
| 4,301,412 | 11/1981 | Hill et al. | 128/637 |
| 4,414,975 | 11/1983 | Ryder et al. | 128/329 R |
| 4,469,110 | 9/1984 | Slama | 128/770 |

*Primary Examiner*—Edward M. Coven
*Attorney, Agent, or Firm*—Hugh D. Jaeger

[57] ABSTRACT

Hand-held shirt-pocket portable medical diagnostic system for checking measurement of blood glucose, urea nitrogen, hemoglobin, blood components or other body qualities. The system includes the engagement of a disposable needle or lance probe package which carries a chemical reagent strip such as blood reacting chemistry. The system includes a pen structure having a visual readout, a microcomputer, and photosensing circuitry which measures the change of color of the blood reacting chemistry of the disposable probe package. The pen also includes a spring arrangement for actuating a needle or lance into the skin for transferring blood from a finger or other area to the chemical reagent strip. A disposable probe structure package includes configurations for transferring of the blood to the reagent strip or the reagent strip to the blood. The pen can also create a vacuum about a time period that the needle is penetrating the skin. The system includes a verification sequence of the electronics, the chemistry of an unused disposable probe package, the presence of blood sample and multiple readings to average results. The system can also be provided with provisions for storing a plurality of readings, communicating with a personal computer, and can act as an alarm and chime to indicate time periods for blood sensing.

7 Claims, 23 Drawing Figures

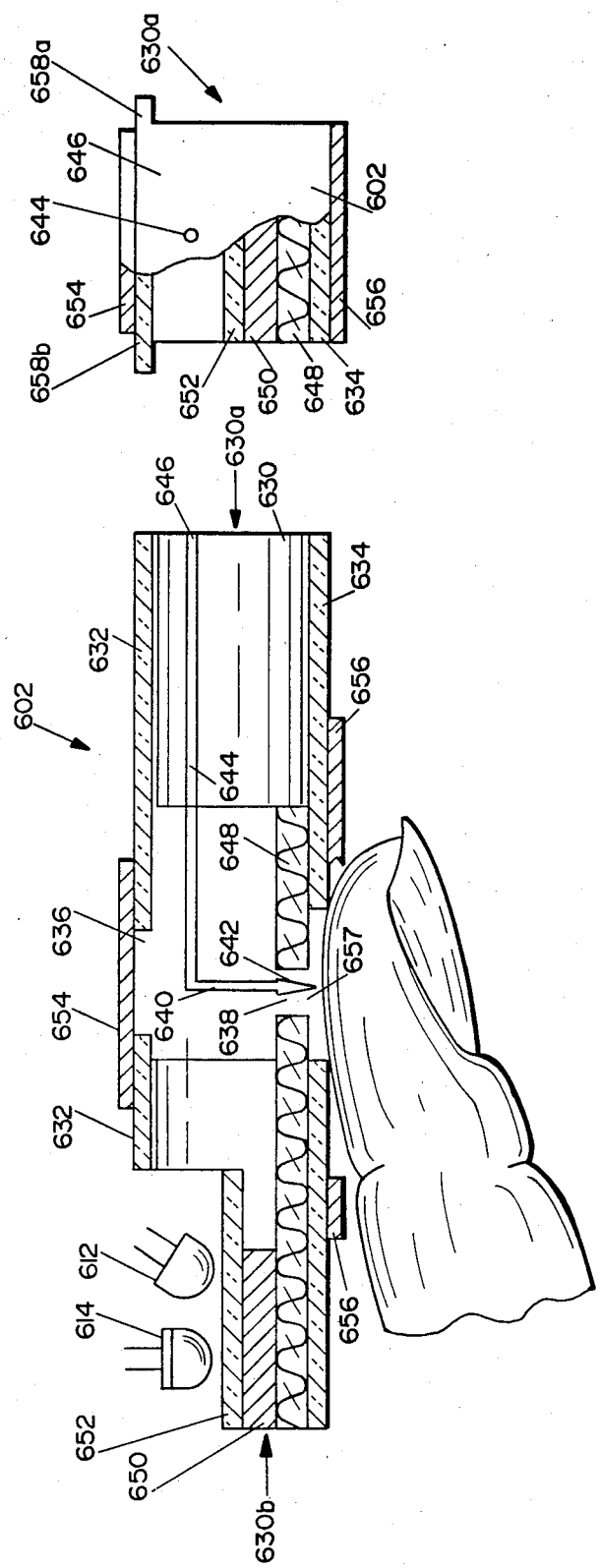

FIG. 22a

| ITEM | RELEVANT GRAPHIC | EVENT | AUDIBLE (BEEPS) | VISUAL DISPLAY | DURATION | NOTES |
|---|---|---|---|---|---|---|
| A. | | INSERT DIAGNOSTIC UNIT INTO HOUSING MEMBER | NONE | NONE | NOT APPLICATION | SWITCH CLOSED...FIRST TIME |
| (1) | | BATTERY OK | NONE | NONE | — | |
| (2) | | BATTERY LOW | NONE | 🔋 | COMPLETION OF SUCCESSFUL OR UNSUCCESSFUL CALIBRATION | IF BATTERY SYMBOL IS DISPLAYED IT MEANS THAT IT IS LOW BUT HAS SUFFICIENT ENERGY FOR ONE(1) MEASUREMENT. BATTERY MUST BE REPLACED BEFORE ADDITIONAL MEASUREMENTS ARE TAKEN; SYSTEM LOCKOUT. |
| (3) | | BATTERY NOT OK | 3 | ⊠ | UNTIL POWER DOWN OR REMOVAL OF DIAGNOSTIC UNIT | BATTERY COULD BE SO LOW THAT THIS STEP MAY NOT BE IMPLEMENTED. |
| B. | | SELF CALIBRATION | NONE | NONE | NOT APPLICABLE | DIAGNOSTIC UNIT FULLY ENGAGED SECOND SWITCH CLOSURE. |
| (1) | | SUCCESSFUL | 1 | - - - | THE THREE(3) DASH LINES: UNTIL POWER DOWN, DISPLAYED GLUCOSE VALUE OR AN ERROR MESSAGE, WHICHEVER OCCURS FIRST. THE NUMERAL: UNTIL POWER DOWN OR UNTIL A SUCCESSFUL OR UNSUCCESSFUL SAMPLE IS OBTAINED, WHICHEVER OCCURS FIRST. | |
| | | | | 2 | | |
| (2) | | UNSUCCESSFUL | 3 | EEE | UNTIL POWER DOWN OR REMOVAL AND REINSERTION OF SAME OR DIFFERENT DIAGNOSTIC UNIT, WHICHEVER OCCURS FIRST. | |

| | | | | |
|---|---|---|---|---|
| C. | 2 | PLACE POINT ON FINGER AND ACTUATE LANCE. | | |
| (1) | 2 | VALID SAMPLE OBTAINED. | 3 | UNTIL GLUCOSE VALUE DISPLAYED. |
| (2) | 2 | VALID SAMPLE NOT OBTAINED WITHIN TEN(10) SECONDS. | 3 EEE 2 | OBTAIN VALID SAMPLE BY MILKING FINGER OR 15 SECONDS ELAPSED TIME, WHICHEVER OCCURS FIRST. |
| (3) | 2 | VALID SAMPLE OBTAINED ON SECOND ATTEMPT. | 3 | UNTIL GLUCOSE VALUE IS DISPLAYED. |
| (4) | 2 | VALID SAMPLE NOT OBTAINED WITHIN FIFTEEN(15) SECONDS | 3 EEE | POWER DOWN OR UNTIL REMOVAL OF DIAGNOSTIC UNIT, WHICHEVER OCCURS FIRST. |
| D. | 2 OR 3 | REMOVE FROM FINGER | NONE | 3 OR EEE2 NOT APPLICABLE |
| E. | 4 | OBSERVE READING | 1 | LLL, HHH, MINIMUM: ONE(1) MINUTE DISPLAYED MAXIMUM: POWER DOWN OR REMOVAL OF DIAGNOSTIC VALUE UNIT WHICHEVER UNIT OF OCCURS FIRST. MEASURE 4 |
| F. | 5 | OBSERVE GLUCOSE READINGS STORED IN FIVE(5) MEMORIES BY REMOVING DIAGNOSTIC UNIT | 1 | MEM n EACH MEMORY DISPLAYED FOR FIVE(5) DISPLAYED VALUES WILL BE IN DISPLAYED SECONDS, THEN POWER DOWN. LIFO SEQUENCE. VALUE, UNIT OF AUDIBLE BEEP(ONE) WILL OCCUR MEASURE AFTER ONE MINUTE FROM ITEM E ABOVE. |

FIG. 22b

GLUCOSE MEDICAL MONITORING SYSTEM

CROSS REFERENCES TO CO-PENDING APPLICATIONS

This application is a continuation-in-part of U.S. Ser. No. 720,906, filed Apr. 8, 1985.

BACKGROUND OF THE INVENTION

1. Field of the Invention

The present invention pertains to medical system for sampling and analyzing blood or any components of the blood for specific readings as to qualities of the blood. One specific use of the present invention is for sensing the accumulation of blood glucose for diabetics. The system is a portable, pocket-size, battery operated, diagnostic system for detection and measurement of blood qualities or of other predetermined qualities.

2. Description of the Prior Art

Prior art blood glucose devices have operated on the principle of taking blood from an individual by a variety of methods, such as by needle or lance. An individual then had to coat a paper strip carrying chemistry with the blood, and insert the blood-coated strip into a blood glucose meter or visual comparison against a color standard. There are numerous blood glucose meters on the market, but are instruments which consume space and are not pocketable. The instruments usually have to be carried in a large handbag, or an individual's briefcase, or left at home such as in the bathroom or the bedroom.

Further, the prior art medical apparatus for sensing blood glucose required that an individual have separately available a needle or lance for extracting blood from the individual, strips carrying blood chemistry for creating a chemical reaction with respect to the blood glucose and changing color, and a blood glucose meter for reading the change in color indicating the blood glucose level. The level of blood glucose, when measured by glucometer, is read from a strip carrying the blood chemistry through the well-known process or reflectometers for glucose oxidation.

Monitor/reagent strip systems that are now available on the market have multiple sequential steps that the patient must follow at exact time intervals. Each step is subject to error by the patient. As in most monitors, it is the patient's responsibility to periodically calibrate the monitor against known color standards; validate the efficacy of their reagent strips and technique by immersing the strips in a control solution of known glucose content; and, then comparing the color change visually against the color standard or by using a calibrated monitor.

In the prior art, the procedure for obtaining accurate results from the time a drop of blood is placed on a reagent strip pad to the time the pad color change is read in the monitor is as follows: The patient must stick himself/herself with a lancet. A drop of blood must be squeezed to the surface of the skin. The drop of blood must then be carefully placed on the reagent pad, making sure to cover the pad completely and the pad must never be touched by the finger of the patient to prevent contamination. Once the sample has been applied to the surface of the reagent pad, the patient must press a timer on the monitor. At the end of the timing, the patient must wipe, blot or wash the strip off, using a careful technique. And for most strips, the patient must place the reacted reagent strip into the monitor, and press a test button or close a hatch to obtain results. Prior art commercially available comparable reagent strips or monitors require operator intervention in a prescribed sequence at exact time intervals. The prior art is subject to operator error, sequence, timing, and technique errors. The prior art reagent strips are also subject to contamination which will affect accuracy of measurement.

The present invention overcomes the disadvantages of the prior art by providing a hand-held pocketable medical system which includes an attachable disposable probe package carrying a chemical reagent chemistry for extracting blood from an individual, delivering the blood to the blood sensing reagent, or vice versa, in the disposable needle package, and resulting in a read-out of a level such as blood glucose. The system includes a microcomputer which is software controlled by an internal program and, of course, provisions can be provided for external programming of the microcomputer. The computer controls all timing functions thereby eliminating human error. The medical system can also assume a rectangular shape and include a slidable diagnostic point for measuring any predetermined quantity which causes a reagent strip reaction.

SUMMARY OF THE INVENTION

One general purpose of the present invention is a portable, shirt-pocket-size, battery-operated diagnostic device/system for use by health professionals and/or lay patients for the detection and measurement of certain selected chemical agents or substances for the purpose of diagnosis and/or treatment of disease. The application is not restricted to use with human beings. It may also be extended to veterinary medicine animals, and can also have uses in the agricultural field, such as measurement of glucose in grapes in the wine industry. One first application is for insulin dependent and non-insulin dependent diabetics for the measurement of glucose in serum, plasma, and/or whole blood. The particular quantity to be measured is glucose through the principles of either reflectance, absorption or potentiometric by electronic circuitry although other quantities can be measured.

Another purpose of the present invention is to provide a hand-held pocketable medical system or measurement system including an engaging disposable needle or lance probe carrying the blood sensing reagent for sensing readings of the blood, such as blood glucose level. The medical system is cost effective and simple to operate by an individual. The reading, such as an individual's glucose level, is displayed on an LCD display on the side of a tubular or rectangular like pen barrel of the medical system which approximates the size of an ordinary ink pen which can be carried in an individual's shirt pocket. The disposable needle probe packages can be carried in a corresponding hollow tubular pencil carrying a plurality of disposable probe packages for use as needed. The tubular or rectangular structure resembling a pen contains the hand-held pocketable medical system, and the tubular or rectangular structure resembling a pencil carries the extra supply of disposable needles. The pen-and-pencil design provides for the utmost peace of mind for the individual.

According to one embodiment of the present invention, there is provided a hand-held pocketable medical system including mechanical or electromechanical pen like structure for actuating a needle in a disposable needle or lance probe package, and for enabling a blood sample inside a finger or on the finger surface to be transferred to blood sensing reagent chemistry, or the blood sensing chemistry to be transferred to the blood. The mechanical structure can assume a variety of spring actuated configurations and can further create a vacuum for drawing the blood outside of the finger. The disposable needle probe package frictionally engages onto a socket at the bottom of the tubular hand-held pocketable medical system such as by snapping, threading, or the like, in place, and is easily releasable and disposable after a single use. The hand-held tubular medical system includes photosensing electronics connected to a microcomputer or custom integrated circuit not only for analyzing the properties of the blood sensing chemistry in the disposable probe package, but also for displaying a readout and storing previous readouts. The electronics includes a verification sequence verifying operability of the electronics including sensing of a low battery condition, verifying the condition of an unused disposable needle package, verifying the presence of a blood sample and subsequently providing multiple readings to provide for an averaging of results. The result will not be displayed until the qualification sequence has been successfully sequenced through verification.

According to other embodiments of the present invention there is provided a diagnostic unit with a wicking action where the wick serves as the transport mechanism for the blood. The wick could also serve as the sterility barrier for a sterilized needle/lance. The wick can be at an angle to the needle/lance and provides for absorption through the wick material.

One significant aspect and feature of the present invention is a hand-held pocketable medical system or measurement system referred to as a "Med Pen" or a "Med Pen Mosquito" which is used to extract a blood sample from the body, subject the sample to chemical analysis, and display the results to the individual. A disposable needle package, referred to as a "Med-Point" carries the blood sensing chemistry consisting of a reagent strip, as well as the needle either for delivering blood to the reagent or for causing the reagent to be delivered to the blood. Additional disposable needle packages can be carried in a corresponding structure similar to that of the medical apparatus referred to as a "Med Pencil."

Another significant aspect and feature of the present invention is a pen like structure which is mechanical, and actuates upon a predetermined amount of pressure being exerted on the skin of an individual's finger. Upon this pressure being sensed, the needle will be actuated down through an individual's skin for the subsequent result of enabling a blood sample to be taken from within the finger or blood sample to occur on the surface of the finger. In an alternative, a button can be pushed actuating the probe into the skin.

A further significant aspect and feature of the present invention is a hand-held pocketable medical system referred to as "Med-Pen Mosquito" which will provide blood glucose readings where the disposable needle probe package carries glucose-oxidase or like chemical reagent, whereby once the blood undergoes a colorometric or potentiometric action proportional to the blood glucose concentration, electronics through the reflectance colorimeter provide for subsequent processing of the photosensing of the blood chemistry for displaying of the results on an LCD display.

A further significant aspect and feature of the present invention is a hand-held pocketable medical system which can be utilized by an individual and only requires the engagement of a disposable needle probe package, subsequent actuation of the apparatus causing a subsequent display on a visual readout for the desired measurement.

Another significant aspect and feature of the present invention is a measurement system which utilizes a slidable disposable diagnostic point unit. The diagnostic point unit carries a spring lance/needle and a transport mechanism for transporting a fluid or liquid to a reagent strip.

Having thus described embodiments of the present invention, it is a principal object hereof to provide a pocketable medical system, including disposable needle packages, which carries blood sensing reagent which engage thereto providing a subsequent readout on a visual display of a quality of the blood. the medical system can be broadly extended to a system for measurement of a quantity of a substance in a particular fluid or material and is not to be construed as strictly limited to medical applications, as the system can be used in industry, agricultural, or even veterinary environments.

One object of the present invention is to provide a hand-held pocketable medical diagnostic system denoted as a Med-Pen Mosquito, disposable medical probe as needle packages referred to as Med-Points or Med-Probes which engage onto the Med-Pen, and a hollow tubular pencil referred to as a Med-Pencil for carrying extra disposable needle Med-Point packages. The disposable needle packages carry blood sensing chemistry or reagent for sensing components of the blood for qualities such as glucose level. Other qualities of any substance can also include urea nitrogen, hemoglobin, alcohol, protein or other qualities of the blood or in other articles such as agricultural products, food, etc.

Another object of the present invention is a Med-Pen which is a reuseable device containing the electronics and software programming, mechanical apparatus, battery(s), sensor(s), and related circuitry that cause the functional operation to be performed. The Med-Point or Med-Probe is a disposable device containing a needle/lance to obtain a blood sample, typically from a person's finger or toe, and a chemical reagent that reacts with the presence of blood as a function of the amount of glucose present in blood. The chemical reagent is sealed inside the Med-Point probe housing or inside a specific housing for the chemical reagent obviating the effects of contamination (from fingers), moisture, and light, thus improving accuracy and precision of measurement by stabilizing the oxidation reduction or chemical reaction of the reagent prior to use. The sensor(s) in the Med-Pen/Point system measure/detect via colorometric and/or potentiometric and/or absorption analysis of the amount of glucose present. This analog data is converted to a digital readout display quantifying glucose in miligrams per deciliter (mg/dl) or MMOL/L.

An additional object of the present invention is a self-contained automatic system. Once the Med-Pen/Point is depressed against the finger (or other area), no further operator intervention may be required depending upon the specific embodiment. All operations and performance of the system are performed automatically and mechanically/electronically in the proper sequence. Accuracy and precision of the measurement is enhanced because errors due to operator interpretation, operator technique, timing of events, and are thereby removed from operator control and influence due to automatic operation. Pressure of the system against a skin surface of a predetermined amount based on spring constants or other predetermined conditions automatically starts the system and sequences the operations dependent upon the specific embodiment.

Still another object of the present invention is a medical system which is software based and software intelligent. The system is self-calibrating through control commands by the software.

A still further object of the present invention is a measurement system with a slidable disposable diagnostic point. The measurement system includes a slidable self-cocking hammer, a push button, release button, and a battery carried in a top compartment.

DESCRIPTION OF THE PREFERRED EMBODIMENTS

Other objects and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 20 illustrates a sectional view of the diagnostic point embodiment for the system of FIG. 19;

FIG. 21 illustrates an end view in partial cross-section of the diagnostic point; and FIGS. 22a and 22b are a system performance chart.

Figure 1:
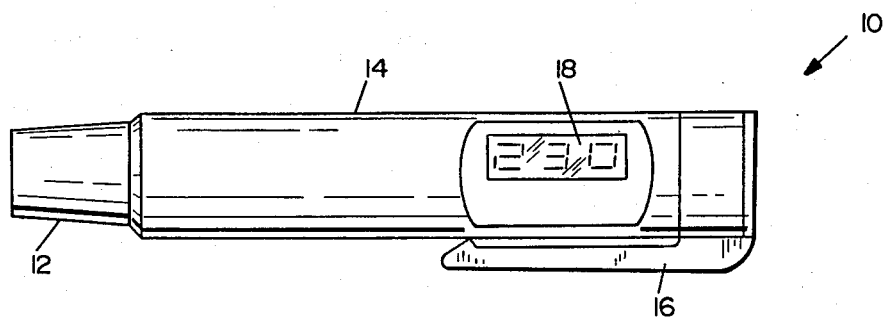
FIG. 1 illustrates a plan view of a hand-held pocketable medical system.

FIG. 1 illustrates a plan view of a hand-held pocketable medical system 10 and a disposable medical probe with a needle or lance or the like carrying blood sensing reagent strip chemistry, all of the present invention. The hand-held pocketable medical system 10 includes a tubular cylindrical pen like member 14 and a clip 16 affixed to the top of the tubular member 14. The disposable medical probe 12 is a narrowing cylinder, and fits into a socket or similar coupling the cylindrical member as later described in detail. A visual electronic readout 18, such as an LCD or the like, including a plurality of digits displays numerical qualities of the blood, as later described in detail.

Figure 2:
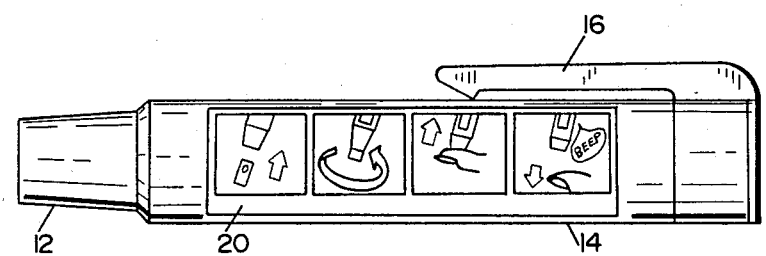
FIG. 2 illustrates an obverse view of FIG. 1.

FIG. 2 illustrates an obverse plan view of FIG. 1 including an instruction panel 21 which can be affixed to the cylindrical tubular member 14 of the system 10.

Figure 3:
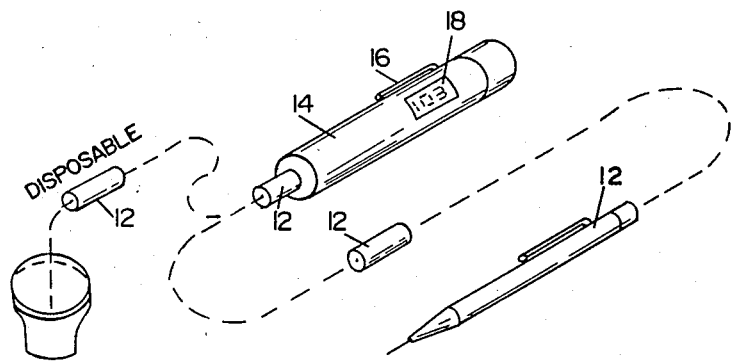
FIG. 3 illustrates a plan view of the system operation.

FIG. 3 illustrates a plan view in perspective of the hand-held pocketable medical system 10, and a disposable medical probe 12 disengaged prior to use and after use. Extra disposable medical probes 12 can be stored in a hollow tubular pencil like cylindrical member 20 which would resemble a pencil like structure.

Figure 4:
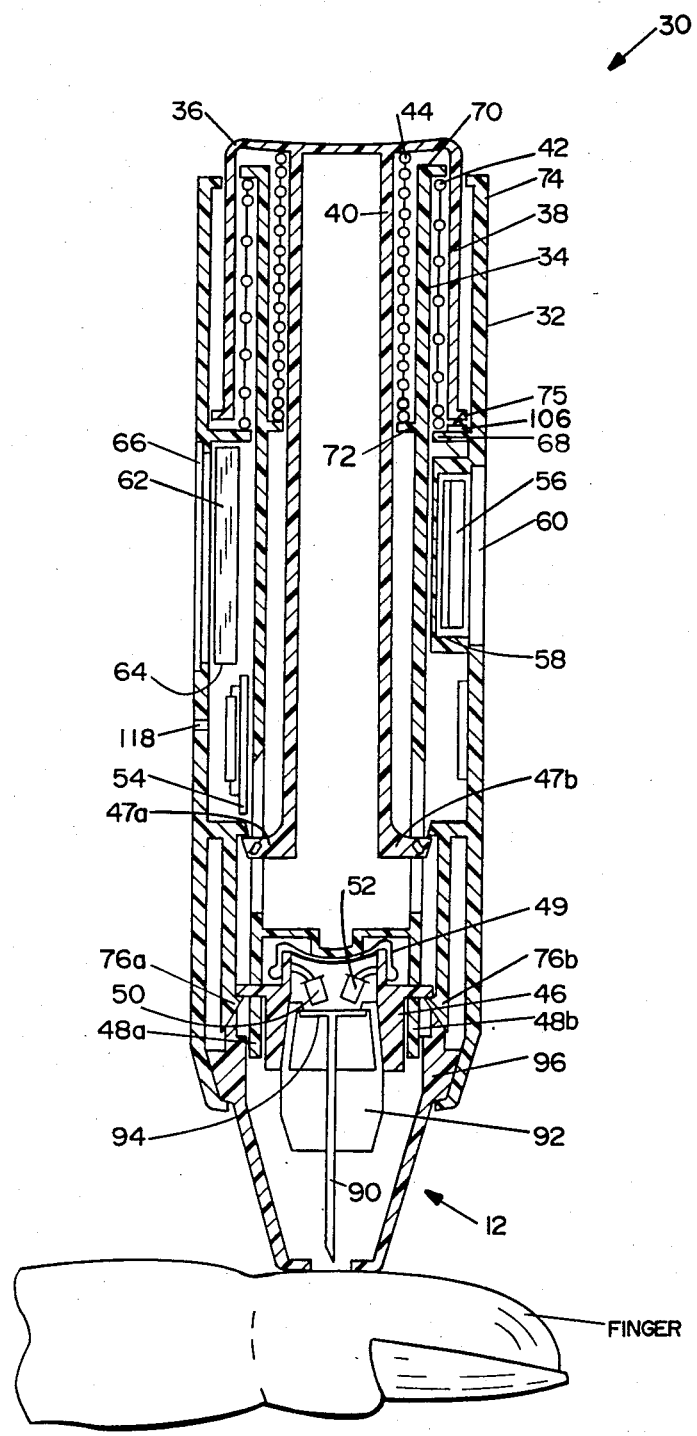
FIG. 4 illustrates a cross-sectional view of a first embodiment.

FIG. 4 illustrates a cross-sectional view of a first embodiment 30 of the medical system 10 prior to finger engagement. The embodiment 30 includes a casing member 32 which is a pen like tubular cylindrical member, and a core portion 34 disposed therein. A button member 36 includes two downwardly extending members 38 and 40 although the button action could be side actuated. An outer spring 42 is disposed between members 38 and 34, and an inner spring 44 is disposed between members 34 and 40. The outer spring 42 is held in position by members 68 and 70. The internal actuating spring 44 is held in position by the lower member 70 and the top of the button 36. Member 74 further limits travel of the button 36 in an upward manner and member 75 limits travel downwardly of button 36. Latch 76a and 76b provide for securing of the diaphragm housing core 46. Latches 47a and 47b are disposed at the lower portion of the downwardly extending member 40. A diaphragm housing core 46 positions in notches 48a and 48b in core part 34. A diaphragm 49 fits over the diaphragm housing core 46. An optical measurement means includes a light source such as LED 50 and a light sensor such as phototransistor 52 mounted in an adjacent and opposed relationship with respect to each other on the walls of the diaphragm housing core 46. The LED 50 and phototransistor 52 connect to an electronics unit 54, as later described in detail. The electronics unit 54 is powered by a battery 56 held in position in battery housing 58 by battery lid 60. A visual display, such as a LCD display 62, positions in a LCD housing 64 and is held therein by a clear viewing lens 66. The disposable probe package 12 includes a needle 90, a probe like supporting structure 92, and a reagent strip 94. The strip 94, while shown in a horizontal configuration, can be in other configurations such as vertical, etc. Release tube 96, which provides means for releasing actuator spring 44, positions in the lower portion of casing 32 and engages the inner surfaces of latches 76a and 76b.

Figure 5:
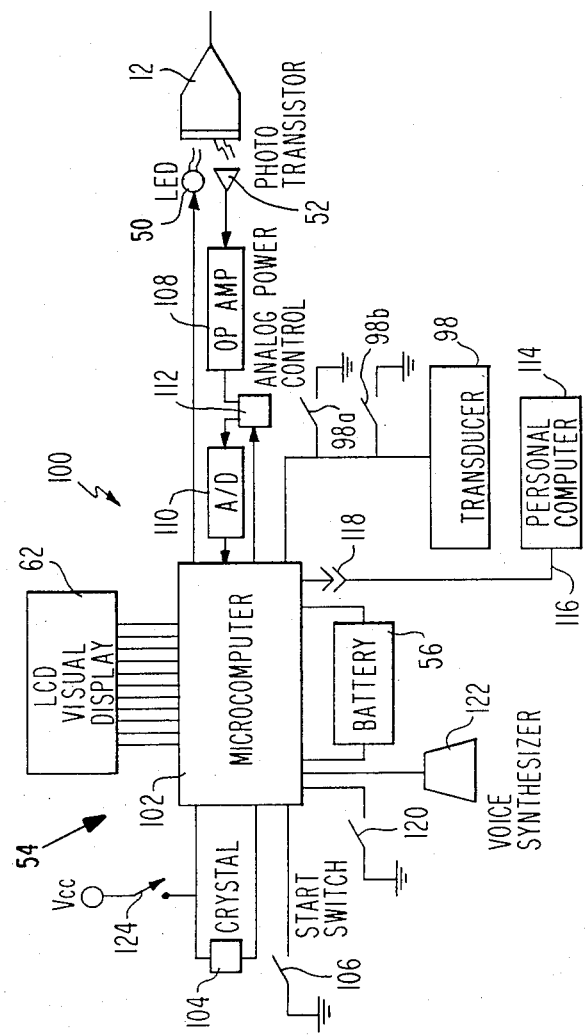
FIG. 5 illustrates an electrical schematic block diagram.

FIG. 5 illustrates an electrical schematic block diagram 100 of the electrical circuitry for the electromechanical structure of FIG. 4. A microcomputer 102 or custom integrated circuit controls operation. A crystal 104 provides the clock signal to the microcomputer 102. A start switch 106 is actuated upon the pressure of the disposable needle 12 against the skin through pressure. An operational amplifier 108 takes an analog signal through to an A/D converter 110. A controller 112 controls power to the op amp 108 and the A/D convertor 110. A piezo electric chiming transducer 98 is connected to an internal clock of the microcomputer for chiming at preset times for medical readings. Switches 98a and 98b set the time. A personal computer 114 can connect by a cable 116 to a plug 118 for outputting stored readings. A recall switch 120 recalls each previous reading as the switch is depressed. A voice synthesizer can also state the reading, the time, and the day. The microcomputer stores software to verify the electronics, verify the calibration procedural steps, and controls the measuring of the qualities as predetermined by the software commands. A power wake up switch or photoswitch 124 turns on the electronics when a probe 12 is inserted into the pen 10.

MODE OF OPERATION

The operation of the hand-held portable medical diagnostic system 10 will now be described in detail, particularly with later reference to sensing of glucose for an insulin type of diabetic individual. This is by way of example and for purposes of illustration only and not to be construed as limiting of the structure or mode of operation of the present invention.

Pushing button 36 loads inner actuator spring 44. The push button 36 locks in place by latch 47a and 47b and holds spring 44 in the compressed state as shown in FIG. 4. Diaphragm 49 is thereby compressed by diaphragm tensioner 51 which is a small projection on the central portion of core 34. By pushing the release tube 96 upward with an individual's finger, from which blood sample is to be taken, latches 76a and 76b are opened, and core 34 is forced downwardly by action of the inner actuator spring 44. Downward movement of core 34 drives the diaphragm housing core 46 with the probe 12 and needle 90 downwardly and simultaneously begins to load outer spring 42. Needle 90 punctures the finger. Downward motion of core 34 opens latches 47a and 47b so that push button 36 can return to its neutral position by being forced upward by further expansion of inner spring 44. Outer spring 42, coaxial to inner spring 44, then can push core 34 upwardly which releases the diaphragm 49, and creates a vacuum in diaphragm housing core 46. The vacuum draws blood up from ruptured capillaries in the finger through the needle 90 into the probe 92 whereupon the blood wets the reagent strip 94. Further upward movement of core part 34 pulls the diaphragm housing core 46 upward so that probe 92 and needle 90 retract from the finger. The diaphragm housing core 46 is then locked in place by the latch 76a and 76b, all mechanical action ends, and all elements are in a neutral position. The blood sample on reagent strip 94 is processed by chemical reaction inside reagent strip 94, and color change of strip is read from the opposite side of reagent strip 94 by reflection of light from LED 50 to the phototransistor 52. The signal is processed in electronics of FIG. 5 as later described in detail, and converted into a numeric value subsequently displayed on LCD 62 which reflects the glucose level of the blood sample. The disposable probe 12 is removed from the device by pulling of the probe causing the skirt of casing member 32 to expand, freeing the probe from the socket.

Further operation of the system is now described. A user attaches a Med-Point probe 12 to the Med-Pen system 10 which accomplishes two functions. The first is the Med-Pen and Med-Point are engaged and made ready for use. The second is the sensor(s) can sense predefined color bands/areas located inside Med-Point as the pen and point are mated, thus automatically calibrating through an algorithm in the software. This self calibration ensures accuracy of measurement before each use; eliminates the need for operator intervention and operator induced error; verifies that the chemical reagent inside Med-Point is the correct color, i.e., unreacted; and, causes the Med-Pen to provide a visual and/or audible alarm if the calibration "acceptance criteria" in the software is not satisfied.

The user places Med-Pen/Point on one's finger or other area from which blood sample is to be taken. The user pushes down one end of Med-Pen and holds down until a tactile response indicates Med-Pen/Point may be removed. The tactile response may be in various forms such as mechanical click from detent action or even an audible beep.

Med-Pen/Point performs all operations in the proper sequence and does not require user intervention. A blood sample is transported by vacuum and/or capillary action to the chemical reagent, and/or chemical reagent is transported to the blood sample on surface/within finger or other areas. The vacuum is created by the mechanical action/design of components in the Med-Pen probe. The capillary action is created by the physical dimensional design of the Med-Point probe as later described. An internal clock/timer in the computer is initiated on pressure being exerted in the system. The chemical reagent reacts with blood/glucose. The electronic sensor(s) can detect coloriometrically and/or photoimetrically the amount of glucose present in the blood sample by measuring the change in color of the chemical reagent and/or the conductivity/impedance of the chemical reagent, respectively. The chemical reaction between the reagent and the blood/glucose is time dependent. Multiple measurements are made at specified time intervals as dictated by an internal clock, thus achieving three results. There is improved accuracy due to the resolution of the measurements over shorter time intervals rather than a single measurement at (x) seconds as in the prior art. There is improved accuracy because multiple measurements can be averaged optionally throughout the high/low readings, etc. for linear or non-linear reactions and/or equations. There is faster response time for operator use; i.e., one doesn't have to wait 30–60 seconds for a reading. The system takes early readings and extrapolates. The Med-Pen system electronics converts the analog data to digital format, and displays a quantitative digital readout of glucose in whole blood expressed in mg/dl or MMOL/L.

The accuracy and precision of measurements is further enhanced because the chemical reaction of the chemical reagent is stabilized. The Med-Point housing or self-contained housing for the reagent chemistry can provide a barrier that insulates the chemical reagent from those parameters that accelerate the reaction; i.e., light, moisture, contaminants from fingertips such as salt, fluoride, etc.

The electronics operates on the reflectance colorometer principal where the blood on the reagent strip undergoes a colorometric or potentiometric reaction proportional to the blood glucose concentration. The electronics provides verification of the system, the chemistry of a reagent of an unused strip, the presence of a blood sample, and provides multiple readings to average the results. Several readings can be taken at specific intervals shortly after the blood reacts with the reagent strip. Once two measurements are made at two distinct time periods, the slope of the reaction of the chemistry can be calculated towards determining an actual final glocose value. In the alternative, the software of the microcomputer can control predetermined samplings at predetermined time intervals and average the result to determine the final glucose reading after a predetermined time period, such as 60 seconds. This improves the accuracy of the final reading. The readings can also be stored and either recalled by a switch on the side of the pen, or recalled by connecting the pen through an innerconnecting cable to a personal computer for outputting the readings for specific times on specific days to a video display or stored for subsequent display or printout.

DESCRIPTION OF ALTERNATIVE EMBODIMENTS

Figure 6:
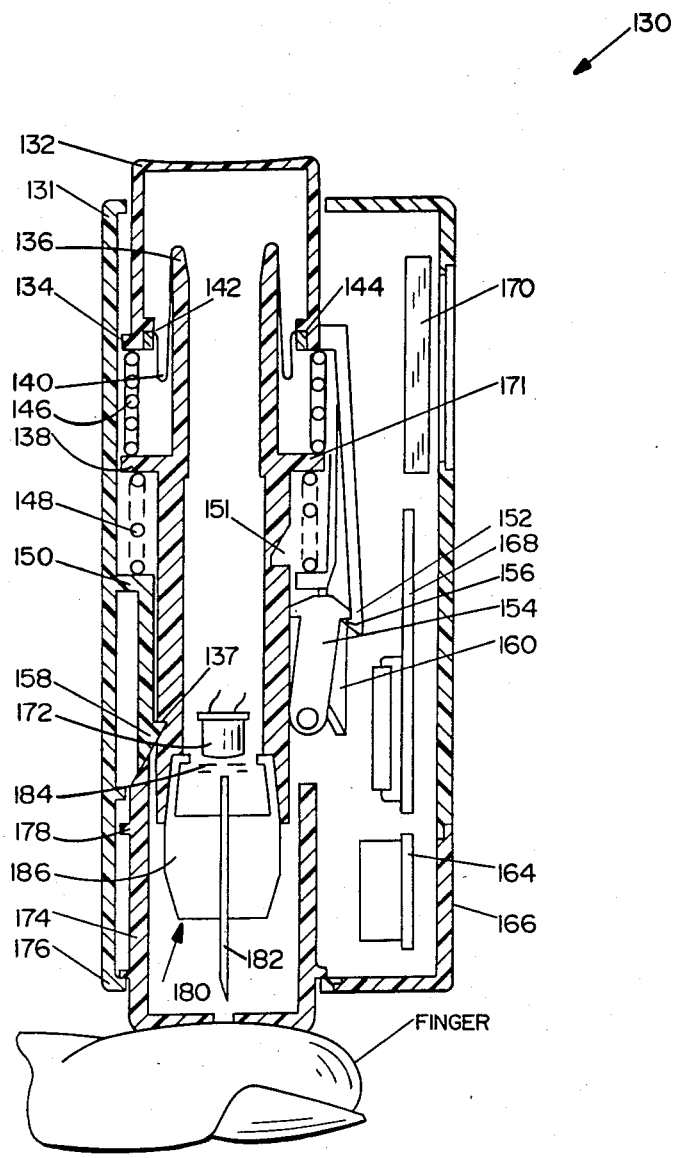
FIG. 6 illustrates a cross-sectional view of a second embodiment.

FIG. 6 illustrates a cross-sectional view of a second embodiment of a medical pen 130. The medical pen 130 includes a housing 131, a button structure 132 including a spring seat 134, a central core 136 including a detent 137, a spring seat 138 and a rolling diaphragm 140 connected between points 142 and 144 of the core 136. Vertically linearlly aligned upper spring 146 and lower spring 148 are between spring actuator seats 134 and 138, respectively, and 138 and 150. Upper latch 152 and lower latch 154 engage at point 156. A latch 158 is part of housing 131. A push button extension 160 extends downwardly from the push button 132. The electronics include a battery 164, a battery cover 166, and the microcomputer assembly 168. An LCD display 170 mounts to the internal portion of a battery cover 166 and includes a clear lens 171. A combined optical sensor 172 provides for illumination, as well as detection, of the color of the chemical change. A release tube 174 includes catches 176 and 178. A probe structure 180 includes a needle 182 and a reagent strip 184 and a probe housing 186.

MODE OF OPERATION

Pushing the button 132 downwardly loads spring 146 and locks button 132 in place by action of latch 158 in detent 137. Air inside button 132 is pushed out through core 136, the porous reagent strip 184, probe 186, and the needle 182. The finger from which blood sample is to be taken pushes the release tube 174 upwards, latch 158 is opened so that loaded actuator spring 146 can drive the core 136 down which loads spring 148 and drives needle 182 of probe 186 into finger. Needle 182 ruptures capillaries in finger. When the core 136 has moved all the way down, latch 154 clips into a detent 151 and releases the latch 152 from engagement at point 156. This releases button 132 which is forced back to the neutral position by spring 146. Upward movement of the button 132 creates a vacuum inside button 132 and the core 136 by action of rolling diaphragm 140, that vacuum then reaches probe 186 and needle 182 through porous reagent strip 184, thus sucking blood from capillaries in the finger into the needle 182 through the probe 186 so as to wet the reagent strip 184. Extension 160 of button 132 retracts latch 154 from detent 151 after a mechanical delay and finite time delay defined by distance between latch 158 and extension 160, thus releasing core 136 which is forced upwards by spring 148 which is then locked in place by latch 158. This action retracts probe 186 with needle 182 from finger.

The blood sample on the reagent strip 184 reacts with the reagents in the reagent strip 184 and the resulting color change is read from the opposite side by optical sensor 172, whose signals are converted by electronics into a numerical readout on display which reflects the glucose level of the blood sample. Disposable probe unit 180 is then removed from device.

DESCRIPTION OF ALTERNATIVE EMBODIMENT

Figure 7:
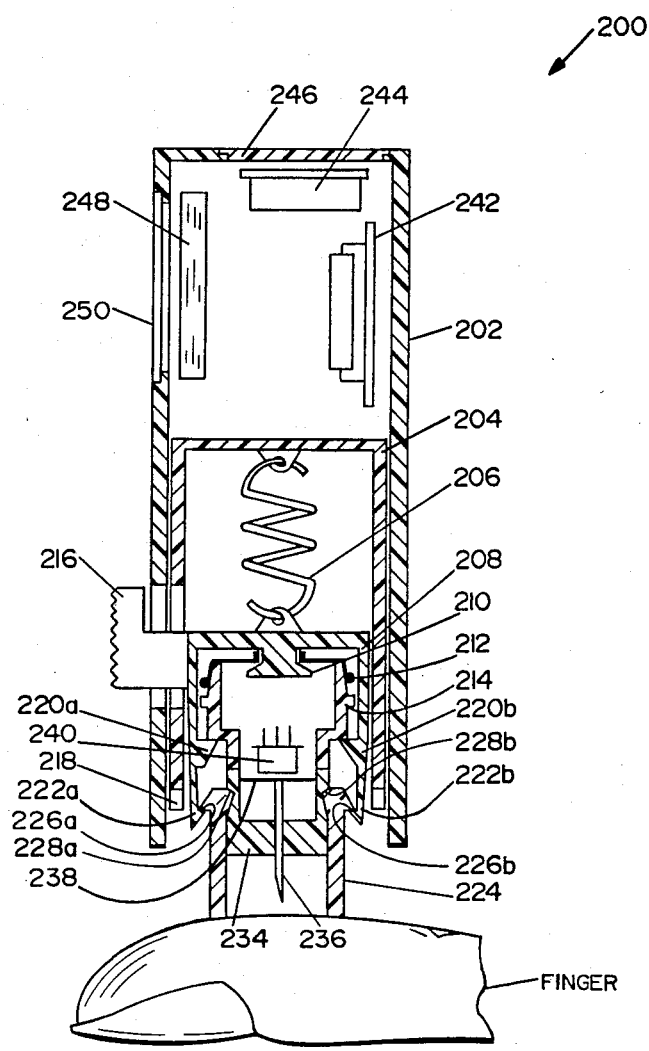
FIG. 7 illustrates a cross-sectional view of a third embodiment.

FIG. 7 illustrates a cross-sectional view of a third embodiment 200. The medical pen 200, an alternative embodiment, includes a casing 202, a spring tensioner 204, a spring 206, a diaphragm tensioner 208, a diaphragm plunger 210, a diaphragm 212, all positioned about a diaphragm housing core 214. This embodiment operates with a single spring 206, which secures between the spring tensioner 204 and and the diaphragm tensioner 208. A slide button 216 secures to the diaphragm tensioner 208. The spring tensioner 204 includes an extension 218 extending downwardly therefrom. The diaphragm tensioner 208 includes upper latches 220a and 220b and lower latches 222a and 222b. A release tube 224 secures at points 226a and 226b to the latches 222a and 222b and at junctions 228a and 228b. The probe 234 includes a needle 236 and a reagent strip 238. The electronics include an optical sensor 240, electronic circuitry 242, a battery 244 with a battery cover 246, and an LCD display 248 with a clear lens 250.

MODE OF OPERATION

The probe 234, needle 236, release tube 224, and reagent strip 238 are a single disposable unit which is inserted into the socket in the pen 200. Upward thrust of extension 218 at release tube 224 during insertion pushes spring tensioner 204 upward which loads spring 206. The disposable unit 234 locks into place by action of latch 222a and 222b. Upward thrust of a finger from which blood sample is to be taken opens junction 228a and 228b between release tube 224 and probe 234 because probe 234 stops at the fixed diaphragm housing core 214. Sudden release of the release tube 224 drives the needle 236 into the finger where it ruptures capillaries. At its upper stop, release tube 224 opens latch 220a and 222b on diaphragm tensioner 208 which is forced upward pulling the diaphragm plunger 210 and the diaphragm 212 upward, thus creating a vacuum inside fixed diaphragm housing core 214. The vacuum reaches needle 236 through diaphragm housing core 214 and draws blood from the finger through the needle 236 which wets the reagent strip 238.

The pen 200 has to be manually removed from the finger and reset by means of the slide button 216. The color change of reagent strip 238 is read from the opposite side by the optical sensor 240, and the electronics unit 242 converts the color change into a numerical readout on the display 248.

DESCRIPTION OF ALTERNATIVE EMBODIMENT

Figure 8:
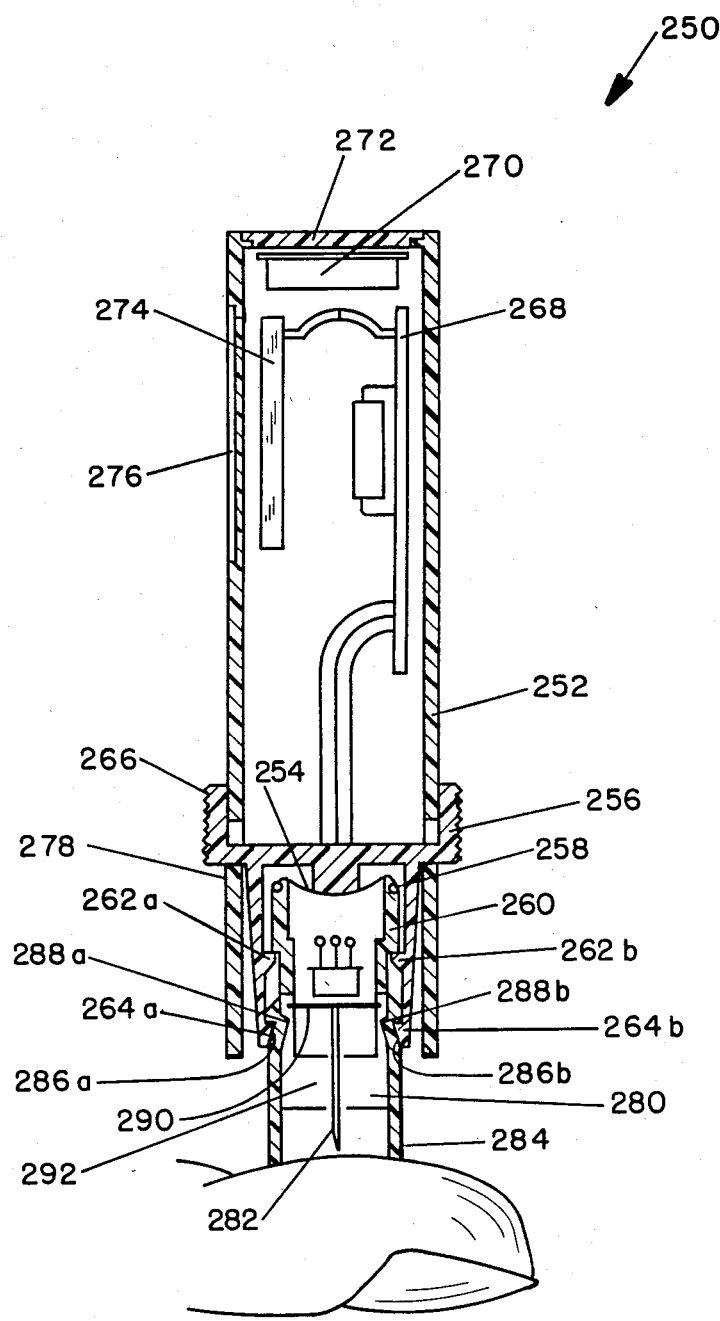
FIG. 8 illustrates a cross-sectional view of a fourth embodiment.

FIG. 8 illustrates a cross-sectional view of a fourth embodiment of a pen 250. The pen 250 includes a casing 252, a diaphragm plunger 254, a diaphragm tensioner 256, and a diaphragm 258. The diaphragm housing core 260 supports the diaphragm 258. Upper latch 262 and lower latches 264a and 264b secure to the diaphragm tensioner 256. A slide button 266 also mounts on the diaphragm tensioner. Internal to the casing 252 are the electronics 268, a battery 270, a screw-on battery cover 272, a display 274, such as an LCD display, and a clear plastic lens 276 inside the casing. Optical sensors 278 connect to the electronics 268. A disposable probe 280 including a needle 282 and a release tube 284 having latch detents 286a and 286b secured to latches 264a and 264b at junctions 288a and 288b. A reagent strip 290 mounts in the probe housing 292.

MODE OF OPERATION

FIG. 8 illustrates the diaphragm tensioner 256 being pushed downward, thus depressing diaphragm 258. Diaphragm tensioner 256 locks into place by the latches 262a and 262b. Probe 280 with the needle 282 and release tube 284 are then inserted and held in place by latches 264a and 264b. Upward thrust of the finger breaks the junction 288 between the probe 280 and the release tube 284 which exposes the needle 282. The needle 282 punctures the finger rupturing the capillaries. At its upper stop, the release tube 284 opens the latches 262a and 262b on the diaphragm tensioner 256 so that by action of the elastic diaphragm 258, the diaphragm tensioner 256 is pushed back. This creates a vacuum in the diaphragm housing core 260 which sucks blood from finger through needle 282 into the probe 280 where the blood wets reagent strip 290. The pen 250 is then manually removed and reset by means of the slide button 266 before the next use. The blood is chemically processed on the reagent strip 290 whose color change is optically read from the opposite side and converted in the electronics unit 268 into a visual readout on display 274. Probe 280 with release tube 284 and needle 282 are held by frictional engagement until removed and disposed of.

DESCRIPTION OF ALTERNATIVE EMBODIMENT

Figure 9:
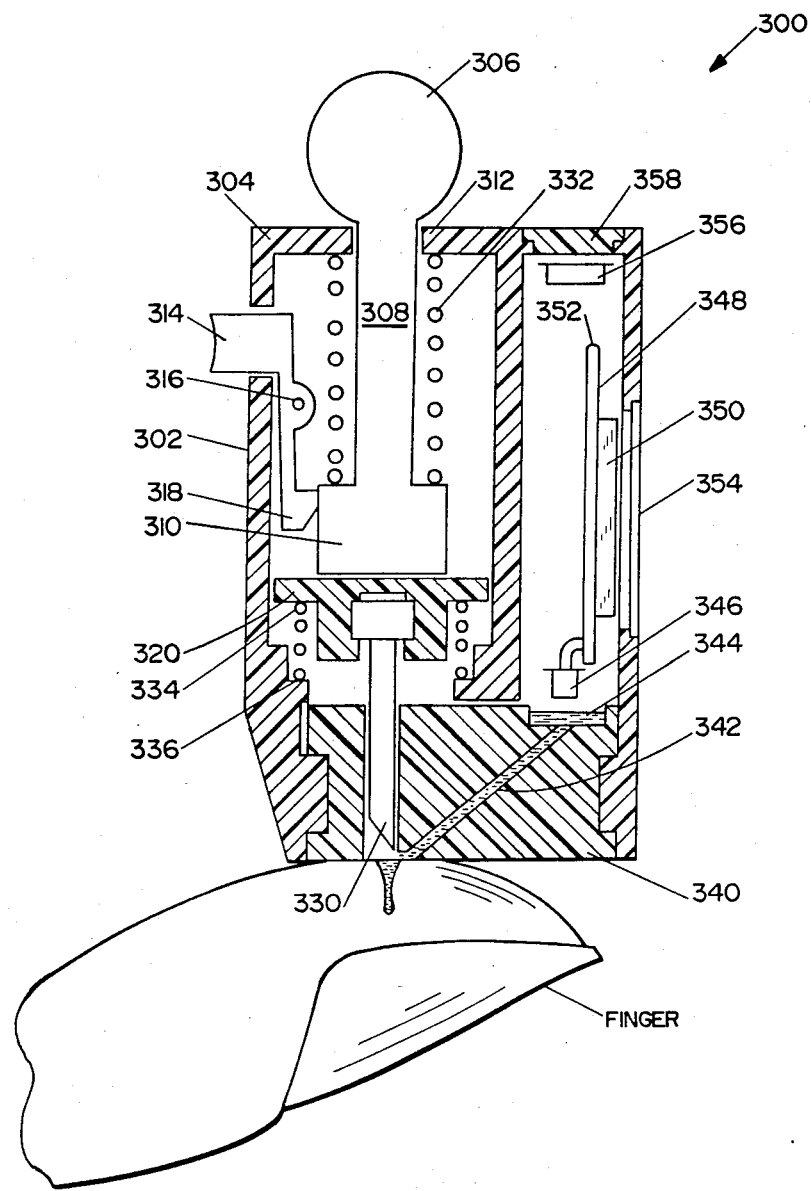
FIG. 9 illustrates a cross-sectional view of a fifth embodiment, a capillary action medical system.

FIG. 9 illustrates a cross-sectional view of a fifth embodiment, a capillary action medical system 300. The capillary action medical system 300 includes a case 302 with a top 304, a knob 306 with a shaft 308, and a plunger 310 fits through a hole 312 in the top 304. A button 314 pivots about a point 316 and includes a latch 318. A lance holder 320 includes a lance 330 therein. An upper spring 332 fits between the top 304 and the top of the plunger 310. A lower spring 334 engages between the bottom of the lance holder 320 and surface 336. A probe 340 includes a capillary duct 342 and a reagent strip 344 therein. Optical sensor 346, microprocessor electronics 348 and an LCD display 350 mount on a board 352. A clear lens 354 fits into the case 302. Likewise a battery 356 applies power to the electronics unit 348 and includes a battery cover 358.

MODE OF OPERATION

Pulling upwardly on knob 306 loads actuator spring 332, and the plunger 310 then locks in place by latch 318. Disposable unit 340 consisting of the lance 330, probe 340 and reagent strip 344 insert into the system 300. The top end of lance 330 is held by lance holders 320. Pushing the button 314 releases the latch 318. The plunger 310 is forced down, hitting lance holder 320. The lance 330 punctures the finger and ruptures capillary blood vessels. By action of the spring 334, the lance holder 320 returns immediately to its neutral position, retracting the lance 330. Blood starts accumulating in the wound channel, and forms a drop on the skin's surface which is drawn into capillary duct 342 by capillary action. Blood rests on the reagent strip 344 and starts the chemical reaction. Color change is then read from the opposite side by the optical sensors 346 connected to the electronics unit 348. The electronics unit converts signals to a digital readout on display 350.

ALTERNATIVE EMBODIMENTS OF MED POINT

Figure 10:
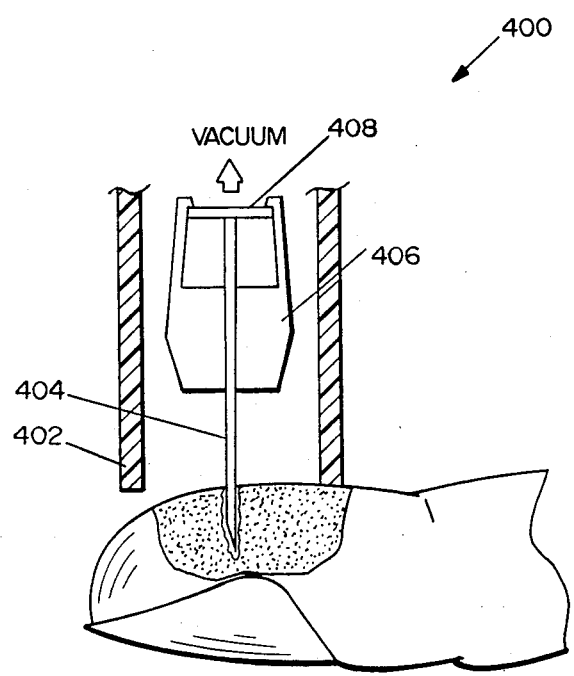
FIG. 10 illustrates a sectional view of a first medical point embodiment.

FIG. 10 illustrates a sectional view of a first embodiment of a medical point 400. A release tube 402 triggers a mechanism in the system 10 which drives a needle 404 into the finger thereby rupturing capillary blood vessels. The blood which accumulates in the wound channel is drawn through the needle 404 into a probe 406 by a vacuum generated in the system, and subsequently onto a reagent strip 408 which can be porous.

Figure 12:
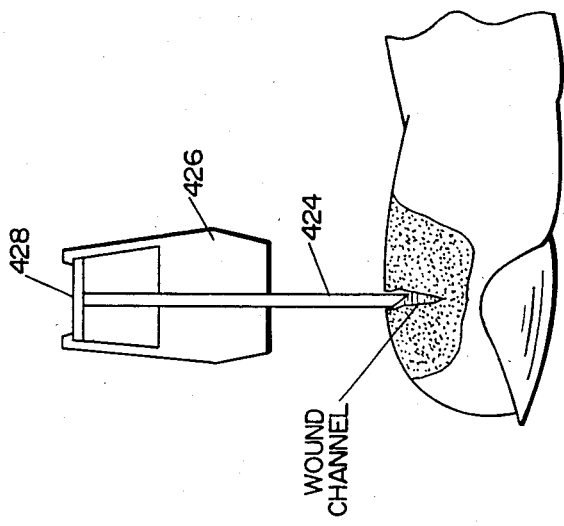
FIGS. 11-12 illustrate sectional views of a second medical point embodiment.
Figure 11:
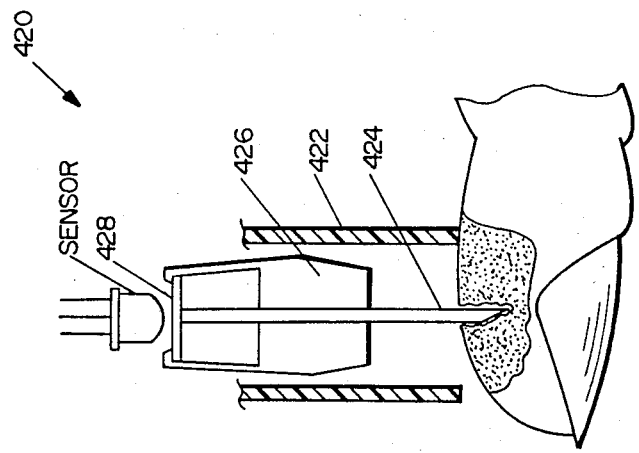

FIGS. 11-12 illustrate a sectional view of embodiments of a medical point 420 having a release tube 422 which is triggered by the system which drives the needle 424 into the finger, thereby rupturing capillary blood vessels. The needle 424 is then retracted halfway in order to allow the blood to accumulate in the wound channel and to avoid being obstructed by the tissue. The blood which accumulates in the wound channel is then drawn through the halfway withdrawn needle into the probe 426 by the vacuum generated in the device and onto the porous reagent strip 428.

Figure 13:
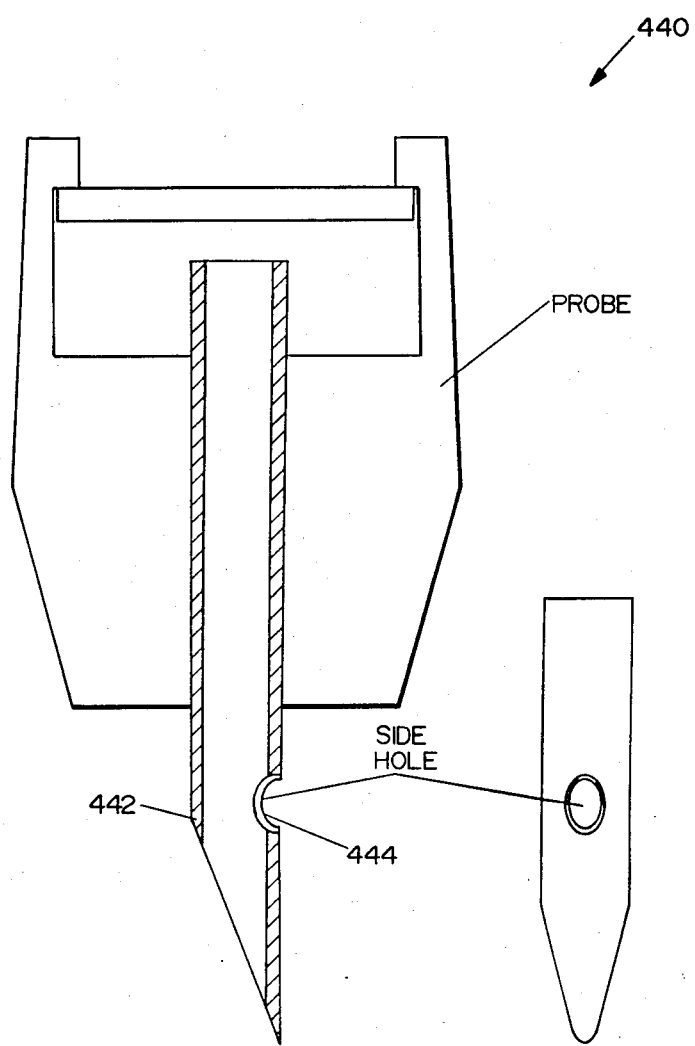
FIG. 13 illustrates a sectional view of a third medical point embodiment.

FIG. 13 illustrates a sectional view of a third medical point embodiment 440 where the needle 442 includes a side hole 444. The needle includes a side hole which provides that the blood can be drawn despite a potentially plugged tip of the needle such as by skin or flesh.

Figure 14:
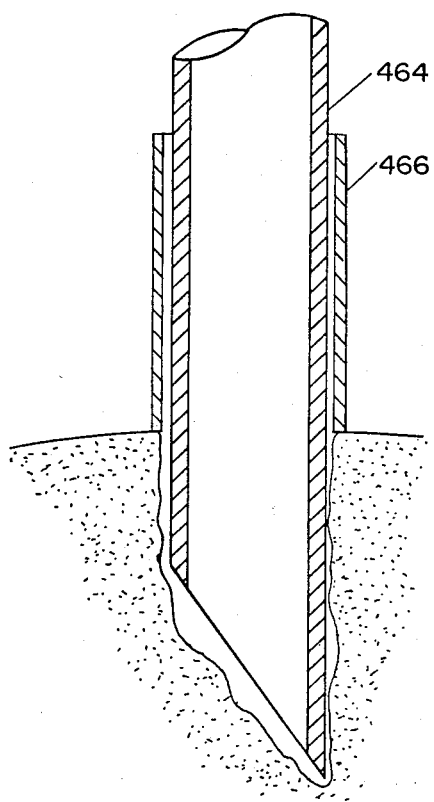
FIGS. 14-15 illustrate a sectional view of a fourth medical point embodiment.
Figure 15:
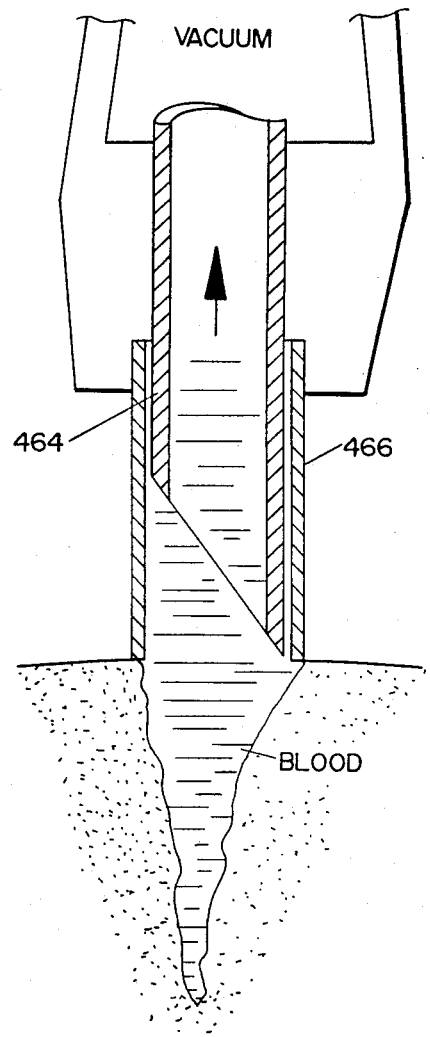

FIGS. 14-15 illustrate sectional views of a fourth medical point embodiment 460 where a needle 464 is enclosed by a side guide tube 466. The side guide tube touches the surface of the finger. After puncturing the finger, the needle 464 is fully retracted in the guide tube 466 and blood is drawn in through the guide tube and the needle as illustrated in FIG. 15. In the alternative, a lance can be utilized in lieu of the needle of FIGS. 14 and 15. The lance can even include a side hole to act as a carrier for carrying the blood in the side hole of the lance.

Figure 16:
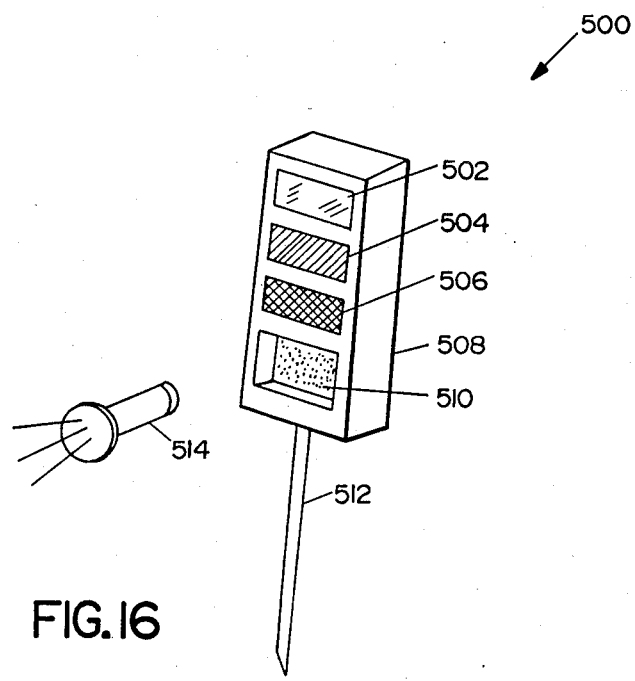
FIG. 16 illustrates a plan view of a system self-calibrating medical point.

FIG. 16 illustrates a plan view of a self-calibration medical point which includes automatic calibration strips for the optical sensors and microcomputer in the system. The medical point 500 includes color strips 502, 504, and 506 about a probe housing 508. Color strips 502-506 have different shades of grey which reflect three defined levels of glucose in the blood for purposes of calibration. During insertion of the Med-Point, the color strips are read by an optical sensor unit 514. Signals are coupled to the electronics unit for calibration of the Med-Point 500 prior the Med-Point reaching its final position. In the final position, the sensor 514 reads the strip 510, which is impregnated with blood through the needle 512.

Figure 17:
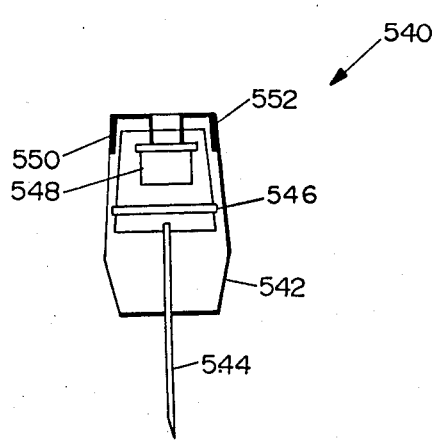
FIG. 17 illustrates a sectional view of a medical probe with self-contained optical sensors.

FIG. 17 illustrates a section view of a medical probe 540 including an optical sensing unit 548 with contacts 550 and 552 mounted in a probe housing 542. A needle 544 connects to the reagent strip 546. The optical sensing unit 548 reads the reagent strip and provides electronic information to the Med-Pen device. The metallic contacts 550 and 552 connect the sensing device to the electronics in the Med-Pen. The entire unit is considered disposable based on low cost of volume integrated circuits.

Figure 18:
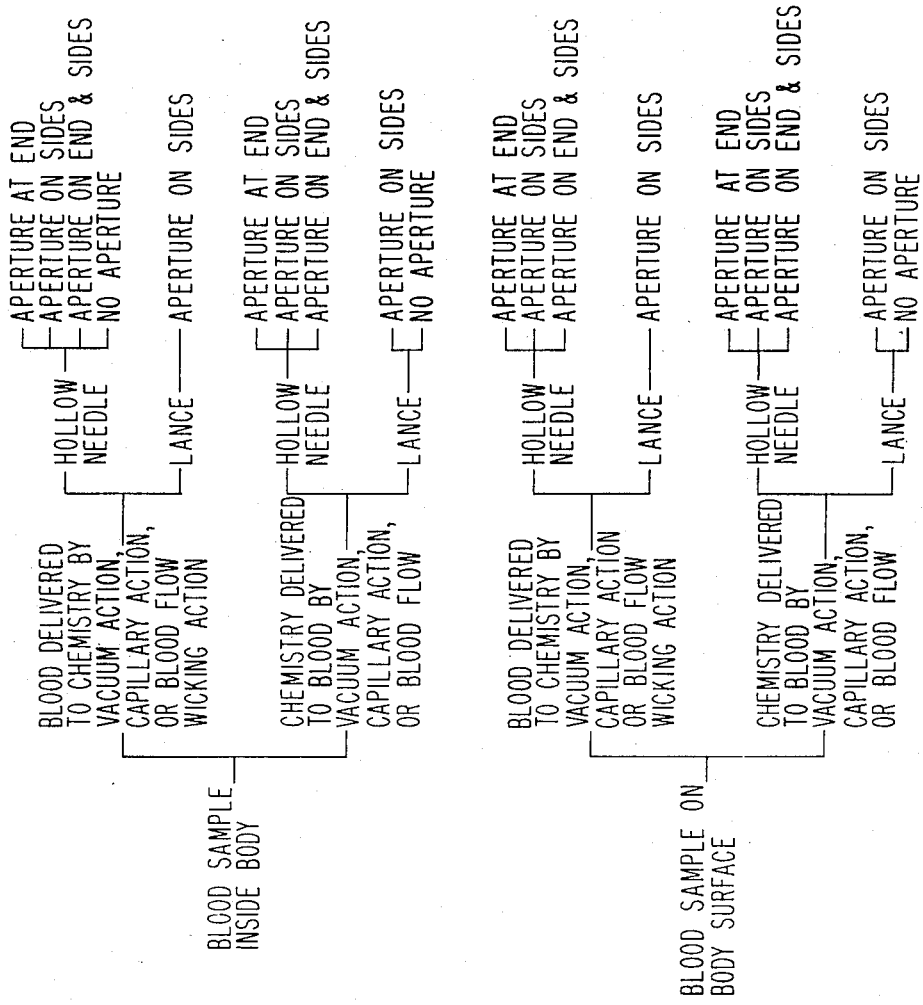
FIG. 18 is a flow chart of blood transfer to the reagent strip.

One alternative embodiment of the present invention is that the blood chemistry can be positioned at the site of the blood rather than taking the blood to the blood chemistry reagent strip. Disposable structures can be provided which would snap in place, although a needle or capillary action would not be required in that the reagent strip would touch blood located on one's skin and commence the process. The mode of operation would be that as previously discussed in pushing the system downwardly so that the release tube would apply upper pressure causing a reagent strip to come into contact with the blood. While all of the previous embodiments have illustrated the blood flowing to the chemical sensing reagent strip, the alternative embodiment can take the reagent strip to the blood, such as by having the reagent strip positioned on a lower portion of the disposable probe. The permutations of whether the blood is taken to the reagent strip or the reagent strip is taken to blood, is illustrated in FIG. 18 in a flow chart diagram. The teachings of the present invention can be expanded such as by having the probe include structure for first pricking and bringing blood from below the skin to the surface of the skin, and then having structure for moving the reagent strip to the blood on the surface of the skin for subsequent transfer of the reagent strip to the blood.

FIG. 18 illustrates the flow chart of the blood or liquid flow in the system. The permutations are outlined in the figure. Another permutation is wicking action which can occur where the blood or liquid is delivered to the chemistry by wicking action or by other processes such as vacuum action, capillary action, natural flow, absorption, or any other flow or transport process.

DESCRIPTION OF MEASUREMENT SYSTEM WITH DISPOSABLE DIAGNOSTIC POINT UNIT

Figure 19:
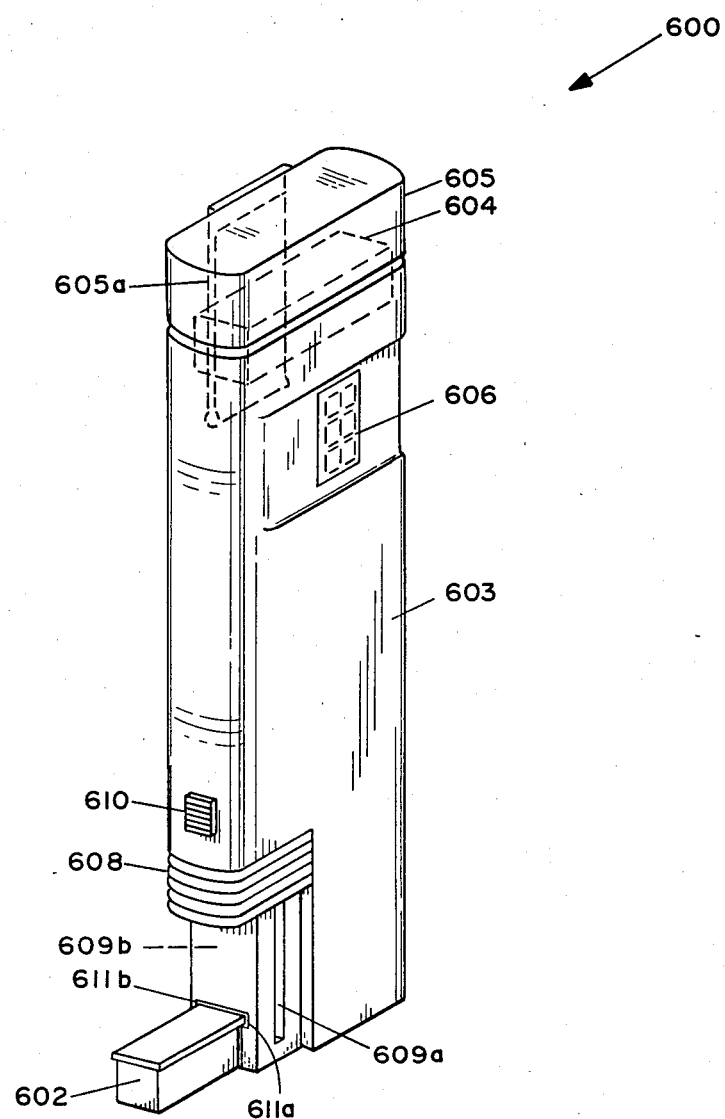
FIG. 19 illustrates a perspective view of an embodiment of a measurement system with a disposable diagnostic point.

FIG. 19 illustrates a perspective view of an embodiment of a measurement system 600 of the present invention, including a slidable disposable diagnostic point unit 602, as later described. The housing 603 is rectangular so as to conveniently accommodate flat pack IC's such as memory. Preferred dimensions are 130 mm length by 24 mm width by 12 mm depth providing a pocket profile by way of example. A battery housing 604 frictionally and electrically engages on the top of housing 603, such as by a snap fit, although other engaging structures can be utilized. A cap 605 carrying a pocket clip 605a engages into the battery housing. A LED display 606 displays the measured quantity, such as glucose. A sliding door 608 in opposing grooves 609a and 609b actuates the electronics, as well as cocking a hammer mechanism, as later described. An actuating button 601 releases the hammer mechanism thereby actuating the lance, as later described. A protective cover approximating the size and shape of point 602 slides into opposing point receiving channel 611a and 611b when a diagnostic point 602 is not inserted into the channel. LED source 612 and photodiode sensor 614 position in the housing, as illustrated in FIG. 20, and corresponds to the electrical circuitry of FIG. 5. Sliding door 608 activates the start switch 106 of FIG. 5.

FIG. 20 illustrates a sectional view of the disposable diagnostic point unit 602 for the system of FIG. 19. The point 602 includes a housing 630, an opaque top cover 632, and an opaque bottom cover 634. A hammer aperture hole 636 is disposed opposite of wick aperture hole 638. A lance 640 with a point 642 and including a spring member 644 secures at one end to the housing 646. Wick member 648, as later described in detail, mounts between members 632 and 634 and within housing members 630a and 630b. The wick 648 transports by wicking action blood or liquid from the lance 640 to a reagent strip 650 protected by a transparent plastic cover 652 where LED 612 and phototransistor 614 measure readings to be processed by internal microprocessor circuitry, as shown in FIG. 5. Optional foil covers 654 and 656 with peel off adhesive can be applied to the top and/or bottom covers 632 and 634 providing sterility for the lance 640. Also, the wicking material member 648 can provide sterility protection to the lance by not having an aperture hole in the material where the material would be a solid piece or material. The wick aperture 638, which is optional, and cover aperture 657 position over the finger in this example for taking a blood sample for determining glucose levels as illustrated in the figure. In the alternative, the apertures could position over an other article for a quantitative analysis, such as a grape, an animal, a solution in an industrial setting, etc.

FIG. 21 illustrates an end view in partial cross section of the diagnostic point unit 602 where all numerals correspond to those elements previously described. The opposing channel members 658a and 658b provide for insertion into channel receptor 611a and 611d and the lower recess area of the rectangular housing 603.

FIGS. 22a and 22b are a system performance chart of events corresponding to the graphics of FIG. 3.

MODE OF OPERATION

The disposable diagnostic point unit provides for personal hygiene and an infection barrier, in that the only part touching the patient is the wick portion of the diagnostic unit 602. The wick portion can be sterilized prior to usage and protected by at least one if not two foil covers 654 and 656 with peel off adhesives. The dimensions of the wick material, as well as the wick material itself, are chosen such as to transfer a minimal amount of fluid from the skin puncturing lance 640 to the reagent material 650. The reagent material 650 is of such a minimal size so as to provide a sufficient photodiode illumination, as well as viewing area. The lance 640 is driven by a hammer cocking mechanism, such as those previously described in FIGS. 4, 6, 7, 8, or 9, to a penetrable depth which can include two settings, one for a child and one for an adult. The specific setting requires deliberate action by an individual. The medical system itself is rectangular in cross-section and light tight for accurate photodiode viewing. The battery housing 604 provides easy replacement of the batteries without even requiring any tools whatsoever.

The sliding door 608 of the diagnostic point unit provides for: 1. insertion and removal of either a protective cover or the disposable diagnostic point unit; 2. cocking of the hammer mechanism; and, 3. activation and setting of the electronics including providing: (a) power on condition, (b) automatic calibration of the electronics, (c) a provision for an audio beep from an acoustic piezo electrical transducer as illustrated in FIG. 5, and (d) a visual display of a power on condition corresponding to graphics on the side of the system, as illustrated in FIG. 2.

The relevant graphics, as well as the event, audio beeps and visual display are further described in FIGS. 22a and 22b with respect to the operation of the medical system or measurement system which are synonymous, and each providing a readout of quantity of a specific quality which is to be measured.

When the hammer mechanism is armed by the sliding door, the push button provides for releasing of the hammer and driving of the lance into the finger once a disposable diagnostic point unit 602 has been inserted into the channels 611a and 611b and positioned into place. The protective cover must be removed, the sliding door moved downwardly and then upwardly to cock the hammer, as well as activate the electrical circuitry for self-calibration as well as measurement, and subsequent insertion of a disposable unit for providing for release of the hammer cocking mechanism which further activates the electronics out of the calibration mode into the sensing mode for photodiode viewing and subsequent computation of the characteristics of the material.

Previously, the electronics has provided for self-calibration through measurement of a predefined color standard, as well as a battery check. After read out is provided of the quantity, such as the glucose level, a button can be pushed to provide the previous readings. The medical system for FIGS. 19-21 provide for slidable action of the disposable diagnostic point unit 602 into a channel, slidable action of a sliding door 608 for the actuation of the electronics, as well as cocking of the hammer, and a push button 610 action for actuation of the hammer.

The wicking unit 648 can include the adhesive-back foil which stabilizes the enzyme in the reagent. The wick 648 can also act as a sterility barrier. The wick can be embedded into a capillary tunnel which operates under an absorption principle. The lance 640, which connects into the housing 630, will include a spring action which is dependent upon the spring modulus of the lance or needle, which includes a right angle or other angular bend between the spring arm and the point. The wicking material 648 will be adjacent to pick up and transporting of the blood from the lance 640 or needle to the reagent strip 652 through a filter 650 for red blood cells. While the wick 648 has been disclosed as having an aperture 638, depending upon the type of specific wicking material, it may not be necessary to have an aperture in the material as the lance 640 or needle could puncture through the wick 648.

FIGS. 22a and 22b illustrate a flow chart including corresponding column entries to graphics of FIG. 2; events; audio beeps, as well as visual displays corresponding to the electronics of FIG. 5; and the duration, as well as application notes. The events, as well as the display duration and application notes, are explanatory in operation of the medical system or measurement system. The system performance chart provides for operational events of the system.

Finally, the wicking action can have a dual purpose in that the wick material can provide a filter media for separating components of a liquid or fluid, in addition to being a sterility barrier for a sterilized needle or lance. One such example of the wicking material acting as a filtering media may be where the wicking material separates certain components of the blood from other components of the blood, by way of example and for purposes of illustration and not to be construed as limiting of the present material. The wicking material can serve more than one purpose, such as wicking for transporting of fluid to chemistry such as a reagent strip, but also can serve as a filter, as well as a sterility barrier.

We claim:

1. Hand-held pocketable measurement system for extraction and analysis of blood in a body, comprising:
   a. pocketable housing member including a spring actuated hammer means in said housing member, optical measurement means including a light source and a light sensor for measuring light emanating from said source and reflected by blood reagent chemistry having a color optical characteristic proportional to the component of the liquid to be measured when in contact with the liquid, said optical measurement means generating an electrical signal responsive to a color change of said blood reagent chemistry and therefore also to the component to be measured, display means responsive to said electrical signal to provide a visual readout representative of the analysis on a display means in said housing member, and channel means for removably receiving a disposable diagnostic unit; and,
   b. disposable diagnostic unit including a unit housing with opposing tabs for slidably and removably engaging said channel means, means supporting said blood reagent chemistry in said unit housing in a position to be sensed by said optical measurement means when said unit housing is engaged within said channel means, said blood reagent chemistry having said color optical characteristics responsive to the component of the liquid to be measured, spring mounted lance means in said unit housing and positioned to be struck by said hammer means, a hole in said unit housing below said lance means, said lance means moving when struck to pierce the body to allow fluid to flow therefrom, and wick means between said lance means and said blood reagent chemistry means for transporting said fluid flowing from within the body to said reagent means, thereby resulting in a color change yielding a responsive optical characteristic which is read by said optical measurement means.

2. System according to claim 1 further comprising cocking means slidably mounted on said housing member for cocking for said hammer means.

3. System according to claim 1 further comprising pushbutton means on a side of said housing member for releasing said hammer means.

4. System according to claim 1 wherein said wick means is positioned across a portion of said base of said unit housing to be penetrated by said lance means when said lance means is struck by said hammer means.

5. System according to claim 1 wherein said wick means selectively transports components of said fluid and provides a filtering action between said fluid and said blood reagent chemistry.

6. System according to claim 1 wherein said blood reagent chemistry is read from a back side by said optical measurement means.

7. Hand-held pocketable measurement system for extraction and analysis of blood in a body, comprising:
   a. pocketable housing member including a spring actuated hammer means in said housing member, optical measurement means including a light source and a light sensor for measuring light emanating from said source and reflected by blood reagent chemistry having a color optical characteristic responsive to the component of the liquid to be measured when in contact with the liquid, said measurement means generating an electrical signal proportional to a color change of said blood reagent chemistry and therefore also to the component to be measured, display means proportional to said electrical signal to provide a visual readout representative of the analysis on a display means in said housing member, and channel means for removably receiving a disposable diagnostic unit; and, b. disposable diagnostic unit including a unit housing with opposing tabs for slidably and removably engaging said channel means, means supporting said blood reagent chemistry in said unit housing in a position to be sensed by said optical measurement means when said unit housing is engaged within said channel means, said blood reagent chemistry having said color optical characteristic responsive to the component of the liquid to be measured, spring mounted lance means in said unit housing and positioned to be struck by said hammer means, a hole in said unit housing below said lance means, said lance means moving when struck to pierce the body to allow fluid to flow therefrom, wick means between said lance means and said blood reagent chemistry for transporting said fluid flowing from within the body to said blood reagent chemistry, and red blood cell filter means for filtering of red blood cells whereby said blood reagent chemistry undergoes a color change yielding a proportional optical characteristic which is read by said optical measurement means from a back side thereof.

* * * * *

UNITED STATES PATENT AND TRADEMARK OFFICE
CERTIFICATE OF CORRECTION

PATENT NO. : 4,637,403

DATED : January 20, 1987

INVENTOR(S) : Fernando S. Garcia et al.

It is certified that error appears in the above-identified patent and that said Letters Patent is hereby corrected as shown below:

ON THE TITLE PAGE ITEM [75], insert

-- David E. Linde --.

Signed and Sealed this

First Day of December, 1987

Attest:

DONALD J. QUIGG

*Attesting Officer*     *Commissioner of Patents and Trademarks*